(12) United States Patent
Harmon et al.

(10) Patent No.: US 10,206,687 B2
(45) Date of Patent: Feb. 19, 2019

(54) HEMORRHAGE CONTROL DEVICE

(71) Applicant: ARMR Systems LLC, Snellville, GA (US)

(72) Inventors: Tyler Jack Prescott Harmon, Cornelia, GA (US); Yegor Podgorsky, Lilburn, GA (US); Chibueze Joseph Ihenacho, Snellville, GA (US)

(73) Assignee: ARMR SYSTEMS LLC, Snellville, GA (US)

( * ) Notice: Subject to any disclaimer, the term of this patent is extended or adjusted under 35 U.S.C. 154(b) by 46 days.

(21) Appl. No.: 15/305,880

(22) PCT Filed: Apr. 21, 2015

(86) PCT No.: PCT/US2015/026953
§ 371 (c)(1),
(2) Date: Oct. 21, 2016

(87) PCT Pub. No.: WO2015/164429
PCT Pub. Date: Oct. 29, 2015

(65) Prior Publication Data
US 2017/0049459 A1 Feb. 23, 2017

Related U.S. Application Data

(60) Provisional application No. 61/982,522, filed on Apr. 22, 2014, provisional application No. 62/070,683, filed on Sep. 4, 2014.

(51) Int. Cl.
*A61B 17/132* (2006.01)
*A61F 5/32* (2006.01)

(52) U.S. Cl.
CPC ...... *A61B 17/1325* (2013.01); *A61B 17/1327* (2013.01); *A61F 5/32* (2013.01)

(58) Field of Classification Search
CPC .............. A61B 17/132; A61B 17/1325; A61B 17/1327; A61F 5/30; A61F 5/32
See application file for complete search history.

(56) References Cited

U.S. PATENT DOCUMENTS 1,299,860 A    4/1919   Plummer
2,702,551 A    2/1955   Hobson
(Continued)

FOREIGN PATENT DOCUMENTS

EP           2 708 215        3/2014
WO    WO-2013/0181118        12/2013

OTHER PUBLICATIONS

International Search Report & Written Opinion on PCT/US2015/026953 dated Aug. 3, 2015.

*Primary Examiner* — Shaun David
(74) *Attorney, Agent, or Firm* — Foley & Lardner LLP

(57) ABSTRACT

The present disclosure discusses systems and methods for controlling a hemorrhage. The hemorrhage control device can include a harness that is worn around an upper junctional area and a lower junctional area of a user. The hemorrhage control device can also include a compression device that is configured to reversibly couple with the harness. The compression device can include a compression puck and a handle. The handle can be coupled with the harness. When rotated the handle can constrict the harness around the upper junctional area or the lower junctional area. The constriction of the harness can also cause the compression puck to compress the upper junctional area or the lower junctional area.

10 Claims, 6 Drawing Sheets

(56) References Cited

U.S. PATENT DOCUMENTS

| Patent/Publication | Date | Inventor | Classification |
|---|---|---|---|
| 4,829,994 A | 5/1989 | Kurth | |
| 4,957,105 A | 9/1990 | Kurth | |
| 5,307,811 A | 5/1994 | Sigwart et al. | |
| 5,383,893 A | 1/1995 | Daneshvar | |
| 5,514,155 A | 5/1996 | Daneshvar | |
| 5,779,657 A | 7/1998 | Daneshvar | |
| 5,799,650 A | 9/1998 | Harris | |
| 7,582,102 B2 * | 9/2009 | Heinz | A61B 17/1322 606/203 |
| 7,604,651 B1 | 10/2009 | Harris et al. | |
| 7,981,135 B2 | 7/2011 | Thorpe | |
| 8,257,732 B2 | 9/2012 | Huey et al. | |
| 8,343,182 B2 | 1/2013 | Kirkham | |
| 8,353,927 B2 | 1/2013 | Lampropoulos et al. | |
| 8,465,514 B1 * | 6/2013 | Rose | A61B 17/1322 606/203 |
| 2003/0176828 A1 | 9/2003 | Buckman et al. | |
| 2005/0273134 A1 * | 12/2005 | Esposito | A61B 17/1322 606/203 |
| 2007/0038243 A1 | 2/2007 | Rutherford | |
| 2007/0289045 A1 * | 12/2007 | Evans | A45F 3/06 2/102 |
| 2008/0312682 A1 * | 12/2008 | Shams | A61B 17/1327 606/203 |
| 2009/0005804 A1 | 1/2009 | Esposito et al. | |
| 2010/0179586 A1 | 7/2010 | Ward et al. | |
| 2010/0286724 A1 | 11/2010 | Rose et al. | |
| 2011/0137336 A1 | 6/2011 | Holcomb et al. | |
| 2011/0270299 A1 * | 11/2011 | Rose | A61B 17/1322 606/203 |
| 2012/0150215 A1 | 6/2012 | Donald | |
| 2012/0310273 A1 | 12/2012 | Thorpe | |
| 2013/0041303 A1 | 2/2013 | Hopman et al. | |
| 2013/0232742 A1 | 9/2013 | Burnett et al. | |
| 2013/0238014 A1 | 9/2013 | Reynolds et al. | |
| 2013/0267994 A1 * | 10/2013 | Crowder | A61B 17/1325 606/203 |
| 2013/0296921 A1 | 11/2013 | Saunders et al. | |
| 2014/0090140 A1 * | 4/2014 | Craig | A41D 1/06 2/2.5 |
| 2016/0345981 A1 * | 12/2016 | Demas | A61B 17/1322 |

\* cited by examiner

HEMORRHAGE CONTROL DEVICE

CROSS-REFERENCE TO RELATED PATENT APPLICATIONS

This application claims priority to U.S. Provisional Patent Application No. 61/982,522 filed on Apr. 22, 2014 and titled "Arterial Compression Tool-Combat Hemorrhage Control Device" and to U.S. Provisional Patent Application No. 62/070,683 filed on Sep. 4, 2014 and titled "Arterial Compression Tool-Combat Hemorrhage Control Device," both of which are herein incorporated by reference in their entirety.

BACKGROUND OF THE DISCLOSURE

A tourniquet can be used to stop or reduce bleeding that can occur as the result of an injury. The tourniquet can be used to control venous and arterial circulation to the cite of the injury. The tourniquet can control the blood flow by applying pressure to the tissue underlying the tourniquet. The applied pressure can occlude the vessels, and prevent or reduce flow therethrough.

SUMMARY OF THE DISCLOSURE

According to one aspect of the disclosure, a hemorrhage control device includes a harness that is configured to be worn around an upper junctional area and a lower junctional area of a wearer. The device also includes a compression device. The compression device can reversibly couple with the harness. The compression device can include a compression puck configured to apply a pressure to at least a portion of an upper junctional area or at least a portion of a lower junctional area. The compression device can also include a handle that is configured to constrict the harness around the upper junctional area or the lower junctional area. The compression device can also include a ratchet mechanism that can enable the handle to rotate in substantially only one direction.

In some implementations, the harness is configured such that the constriction of the harness can cause the compression puck to apply a pressure to a portion of the upper junctional area or a portion of the lower junctional area. The harness can include one or more modular lightweight load-carrying equipment (MOLLE) loops to which the handle can reversibly couple. In some implementations, the handle is configured to constrict the harness with a windlass mechanism. A bottom surface of the compression puck can be textured.

The handle of the device can reversibly coupled to the compression puck. The ratchet mechanism can include a drawn-cup needle roller bearing. In some implementations, the device includes a second compression device that is configured to reversibly couple with the harness. The lower junctional area can include at least one of a femoral artery, an iliac artery, and an aortic artery of the user, and the upper junctional area can include at least one of an axillary artery and a subclavian artery of the user.

According to another aspect of the disclosure, a method for controlling a hemorrhage can include providing a hemorrhage control device. The device can include a harness that is configured to be worn by a user around an upper junctional area and a lower junctional area. The device can also include a compression device that is configured to reversibly couple with the harness. The compression device can also include a compression puck that is configured to apply a pressure to at least one of a portion of the upper junctional area or a portion of the lower junctional area. The compression device also includes a handle that can be configured to constrict the harness around the at least one of the upper junctional area and the lower junctional area. The compression device can also include a ratchet mechanism that is configured to enable the handle to rotate in substantially only one direction. The method can also include coupling the handle of the compression device to the harness, and then rotating the handle of the compression device.

In some implementations, the constriction of the harness causes the compression puck to apply the pressure to a portion of the upper junctional area or a portion of the lower junctional area. The method can also include coupling the handle to the compression puck. In some implementations, the harness can include one or more MOLLE loops to which the handle is reversibly coupled.

In some implementations, the method also includes coupling a handle of a second compression device to the harness, and rotating the handle of the second compression device. The handle can constrict the harness with a windlass mechanism. The ratchet mechanism can include a drawn-cup needle roller bearing. The upper junctional area can include at least one of an axillary artery and a subclavian artery of the user, and the lower junctional area can include at least one of a femoral artery, an iliac artery, and an aortic artery of the user.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

In some implementations, the systems and methods described herein are configured to simultaneously apply a compressive pressure to tissue, such as that at a junctional area, and a constrictive pressure around the tissue to control venous and arterial circulation. As an overview, the system can include a harness that is worn by the wearer prior to an injury. A compression device can be coupled to the harness. As a user rotates the handle of the compression device, the harness spools around the compression device. The spooling of the harness constricts the harness around the target tissue and simultaneously drives the compression device into the tissue.

Figure 1:
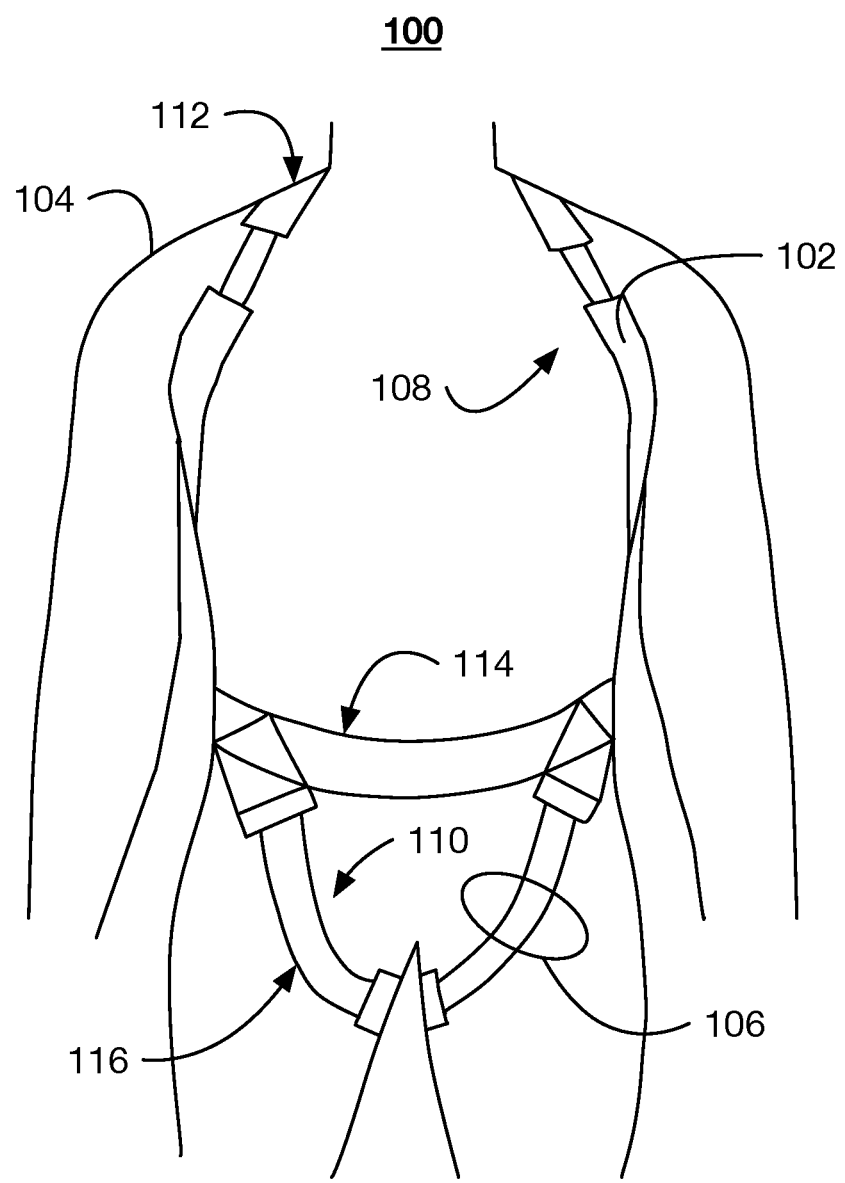
FIG. 1 illustrates an example system for hemorrhage control.

FIG. 1 illustrates an example system 100 for hemorrhage control. The system 100 includes a harness 102 that is worn by a wearer 104. The harness 102 is worn by the wearer 104 around at least one upper junctional area 108 and at least one lower junctional area 110. The system 100 also includes at least one compression device 106 that is reversibly coupled to the harness 102. As illustrated in FIG. 1, the compression device 106 is coupled to the harness 102 at one of the wearer's lower junctional areas 110. As further described below, the compression device 106 includes a compression puck that can be used to apply pressure to the wearer's upper junctional area 108 or lower junctional area 110. A plurality of compression devices 106 can be coupled to the harness 102 at any one time. For example, a plurality of compression device 106 can be applied over a single junctional area, one compression device 106 can be applied at a plurality of junctional areas, or a plurality compression device 106 can be applied at a plurality of junctional areas. The compression device 106 also includes a handle that is configured to constrict the harness 102 around the wearer's upper junctional area 108 or lower junctional area 110 when rotated. The constriction of the harness can cause the depression of the compression puck into the wearer's upper junctional area 108 or lower junctional area 110. The compression device 106 can also include a ratchet mechanism that enables the handle to rotate in substantially only one direction and maintains the constriction of the harness 102 around the wearer's upper junctional area 108 or lower junctional area 110.

The system 100 includes the harness 102. The harness 102 is described further in relation to FIGS. 2-4. As an overview, the harness 102 is worn by the wearer 104 prior to use of the system 100. For example, the harness 102 may be worn by a soldier as part of the everyday combat dress. In this example, if the solider is injured and requires a tourniquet, the compression device 106 can be coupled to the harness 102 and used to apply pressure to the soldier's wounds or to injured blood vessels. Wearing the harness 102 prior to the need for a tourniquet can reduce the total amount of time required to stop (or reduce) blood flow to an injury because the soldier is already wearing the harness 102 and a constriction mechanism (e.g., a strap or cuff) does not also need to be applied to the soldier. In some implementations, all or part of the harness 102 can be applied to wearer after the injury. For example, the harness be worn around the waist and shoulders of a wearer and the leg straps of the device may be deployed after the injury. The harness 102 can be worn and encircle (partially or totally) at least one upper junctional area 108 and at least one lower junctional area 110. In some implementations, the harness 102 may only encircle one or more upper junctional areas 108 or one or more lower junctional areas 110. A junctional area of the wearer 104 includes the areas of the wearer's body near where the trunk of the wearer 104 joints the appendages, such as the arms and legs. The upper junctional areas 108 can include the areas of the wearer's body where the trunk meets the arms, and the lower junctional areas 110 can include the areas of the wearer's body where the trunk meets the legs. Major arteries and veins can pass through the junctional areas of the wearer 104. For example, the femoral, iliac, and aortic arteries can pass through the lower junctional area 110, and the axillary and subclavian arteries can pass through the upper junctional area 108. In some implementations, the harness 102 is configured to cross other major and minor arteries and veins. As illustrated in FIG. 1, the harness 102 includes an over-the-shoulder component 112 that encircles the wearer's two upper junctional areas 108. The harness 102 also includes a waist component 114 with two leg straps 116 that encircle each of the wearer's lower junctional areas 110.

The harness 102 can be manufactured from a nylon webbing, polypropylene, or a similar fabric. In some implementations, the harness 102 includes pouches constructed from a rip-stop fabric, such as rip-stop nylon fabric. The pouches can be used to store the leg straps 116 when not in use. The various components of the harness 102 can be sewn together with treads containing, nylon, cotton, polyester, viscose, rayon, or a combination thereof. In some implementations, the harness 102 is constructed to meet military specifications. The straps of the harness 102 can be between about 1 inch and about 3 inches, between about 1 inch and about 2 inches, or between about 1 inch and about 1.5 inches. In some implementations, different portions of the harness 102 are constructed with different sized straps. For example, portions of the harness 102 that interface with the compression device 106 can be manufactured from 1 inch wide straps while the portions of the compression device 106 not intended to interface with the compression device 106 can be manufactured from 1.5 inch wide straps. In some implementations, the harness 102 is sized according to the size of the wearer 104. In other implementations, the harness 102 can be manufactured in specific sizes (e.g., small, medium, and large). The harness 102 can include one or more buckles and fasteners, such as a snap-fit buckle, that enables to wearer 104 to adjust the fit of the harness 102 and that can also facilitate the wearer 104 in putting on the harness 102. For example, rather than stepping through the loops created by each of the leg straps 116, the leg straps 116 can include snap-fit buckles that enable to wearer 104 to pull the leg straps 116 forward and under the leg from their attachment point on the side or back of the waste component 114 and connect the leg straps 116 to the front of the waist component 114.

Figure 2:
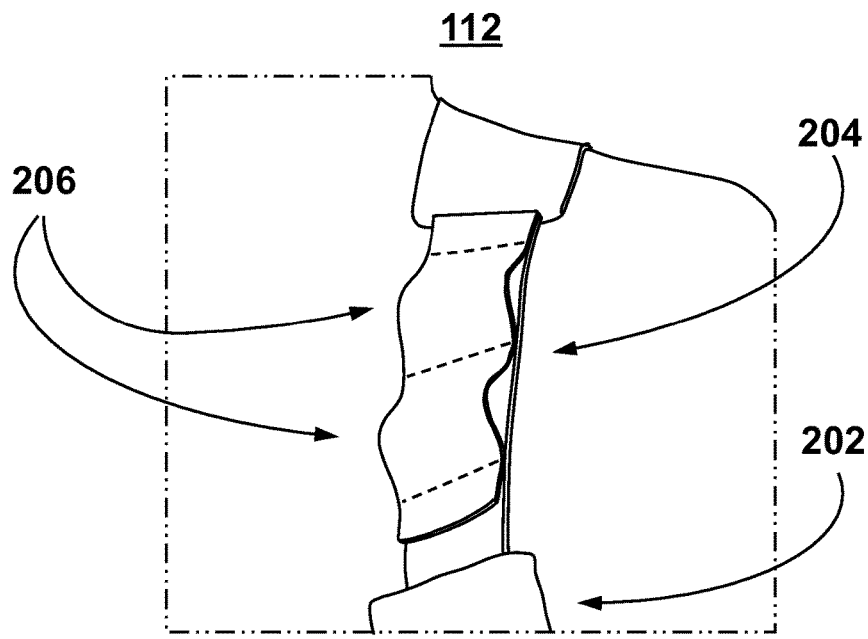
FIGS. 2-4 illustrate enlarged views of an example harness for use in the system illustrated in FIG. 1.

FIG. 2 illustrates an enlarged view of the over-the-shoulder component 112 of the harness 102. As described above, in some implementations, the harness 102 can include different widths of strap for the portions of the harness 102 that interact with the compression device 106. FIG. 2 illustrates that the harness 102 includes a wider portion 202 and a narrow portion 204. The narrow portion 204 is configured to interact (e.g., reversibly couple) with the compression device 106. The narrow portion 204 (or other portions of the harness 102) can include modular lightweight load-carrying equipment (MOLLE) loops 206 to facilitate the coupling of the compression device 106 with the harness 102.

Figure 3:
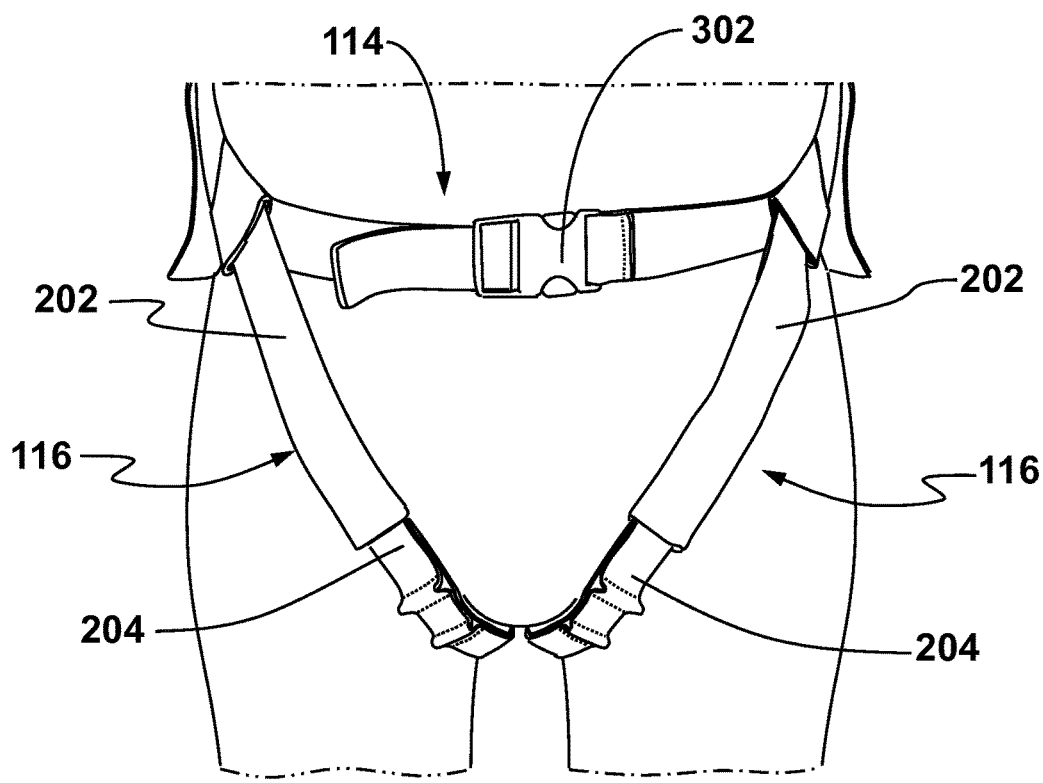

FIG. 3 illustrates an enlarged view of the lower, front portion of the harness 102 when worn by the wearer 104. The lower portion of the harness 102 includes the waist component 114 with two leg straps 116 that wrap around each of the lower junctional areas 110. The waist component 114 includes a snap-fit buckle 302 that enables the wearer 104 to secure and tighten the waist component 114 about the wearer's abdomen. Each of the leg straps 116 can include a wider portion 202 and a narrow portion 204.

Figure 4:
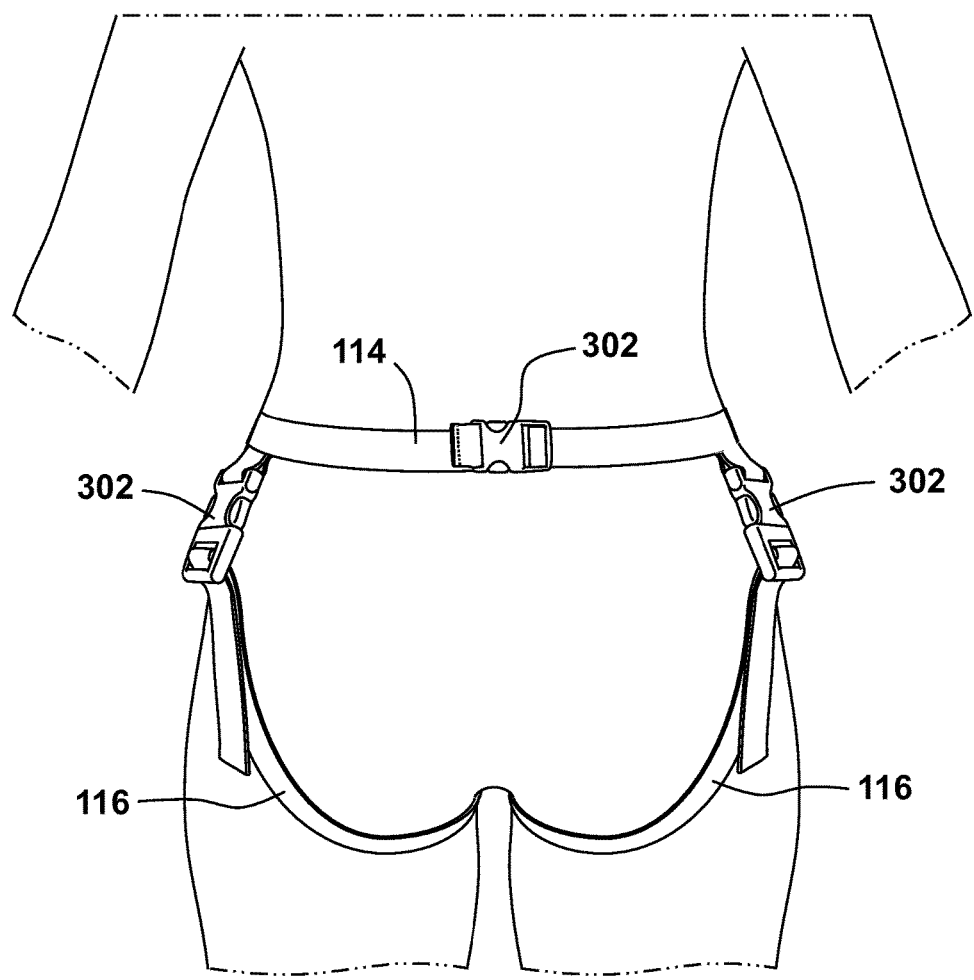

FIG. 4 illustrates an enlarged view of the lower, back portion of the harness 102 when worn by the wearer 104. The back of the waist component 114 can include a buckle 302. In some implementations, the harness 102 can include a plurality of buckles that enable the harness 102 to be quickly removed from the wearer 104. For example, the plurality of buckles can facilitate medical professionals or others in quickly removing the harness 102 during emergency or other situations. FIG. 4 also illustrates the buckles 302 can be included in the leg straps 116 for easy deployment of the leg straps 116. In some implementations, the waist component 114 includes one or more pouches to store the leg straps 116 when the leg straps 116 are not wrapped around the lower junctional areas 110 of the wearer 104.

Figure 5:
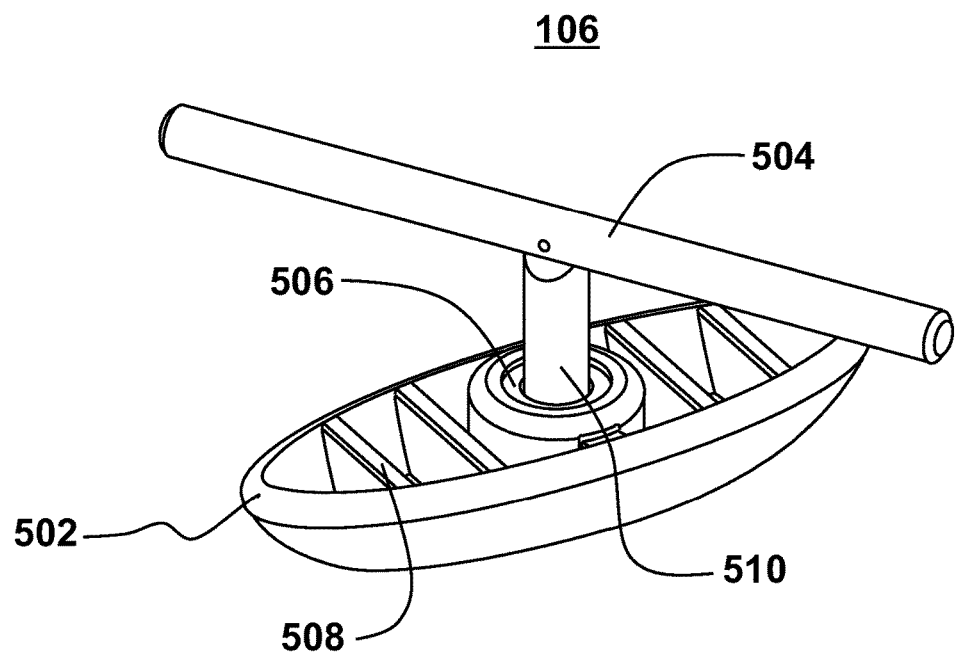
FIG. 5 illustrates a perspective view of an example compression device for use in the system illustrated in FIG. 1.

FIG. 5 illustrates a perspective view of the compression device 106. The compression device 106 includes a compression puck 502 (also referred to as a puck 502) that is configured to apply pressure to a junctional area of the wearer 104. The compression device 106 also includes a handle 504. The handle 504 is coupled to the puck 502 with a ratchet mechanism 506.

The puck 502 of the compression device 106 can be oval shaped. The puck 502 can taper toward the base of the puck 502. In other implementations, the puck 502 is circular, square, rectangular, or any other shape that can distribute pressure to the arteries to substantially constrict the flow of blood through the arteries. The corners of the puck 502 can be rounded to reduce the chance of injuring the wearer 104 when the puck 502 is compressed into the junctional area of the wearer 104. The puck 502 can includes a plurality of support structures 508, such as ribs, that provide rigidity to the puck 502. In other implementations, the puck 502 can be a solid block of material. The puck 502 can be manufactured from acrylonitrile butadiene styrene (ABS) plastic, aluminum, stainless steel, rubber, glass filled nylon, carbon fiber, polyether ether ketone (PEEK), nylon, 3-D printed materials, polyethylene terephthalate (PET). The puck 502 can be machined from a bulk material, 3D printed, or injection molded. In some implementations, the bottom of the puck 502 (e.g., the surface of the puck 502 in contact with the wearer 104) is textured so that the puck 502 stays in place when pressed into the wearer 104. For example, the bottom of the puck 502 can include knurling or a soft textured pad that aids in the grip of the puck 502. In some implementations, the length of the puck 502 is between about 2 inches and about 8 inches, between about 3 inches and about 7 inches, or between about 4 inches and about 6 inches. In some implementations, the width of the puck 502 can be between about 1 inch and about 8 inches, between about 2 inches and about 7 inches, or between about 3 inches and about 6 inches. For example, an oval puck may be about 4.25 inches long by about 1.5 inches wide. In some implementations, the puck 502 is between about 0.5 inches and about 3 inches, between about 0.5 inches and about 2 inches, or between about 0.5 inches and about 1 in tall.

The compression device 106 can also include a ratchet mechanism 506. The ratchet mechanism 506 can be configured to enable the handle 504 to rotate in substantially only one direction. For example, as a user rotates the handle 504 clockwise, the ratchet mechanism 506 can prevent the handle 504 from rotating counterclockwise when the user releases the handle 504. The ratchet mechanism 506 can enable the pressure applied by the puck 502 and the constrictive pressure applied by the harness 102 to be maintained without the need for a user to hold the handle 504 in place. In some implementations, the ratchet mechanism 506 includes a drawn-cup needle roller bearing, ball roller bearing, threaded mechanisms (e.g., screws), ratchets with a catching teeth mechanism. The compression device 106 can also include a securing latch, pin, or strap that can be coupled to the handle 504 (or other component of the compression device 106) to prevent the handle 504 from unwinding after a portion of the harness 102 is wound around the handle 504. In some implementations, the puck 502 can include a locking mechanism in place of, or in addition to, the ratchet mechanism 506. For example, the user may be able to rotate the handle 504 clockwise and then lock the handle 504 in place with a pin that prevents the handle from rotating counterclockwise.

The compression device 106 can also include the handle 504. The handle 504 (and shaft 510 thereof) can be manufactured from stainless steel, aluminum, titanium, rubber, glass filled nylon, carbon fiber, polyether ether ketone (PEEK), nylon, 3-D printed materials, polyethylene terephthalate (PET), or a combination thereof. In some implementations, the length of the handle 504 is between about 3 inches and about 8 inches, between about 4 inches and about 7 inches, or between about 5 inches and about 6 inches long. The diameter of the handle 504 can be between about 0.25 inches and about 1 inch, between about 0.25 inches and about 0.75 inches, or between about 0.30 inches and about 0.50 inches wide. In some implementations, the height of the shaft 510 of the handle 504 is between about 1.0 inches and about 4 inches, between about 1.5 inches and about 3 inches, or between about 1.5 inches and about 2 inches tall. In some implementations, the shaft 510 and handle 504 are configured to reversibly mate with one another. For example, the top of the shaft 510 may be keyed to mate with a hole in the bottom of the handle 504. This may enable the handle 504 be removed from the compression device 106 for storage, and then coupled with the shaft 510 just prior to use.

Figure 6:
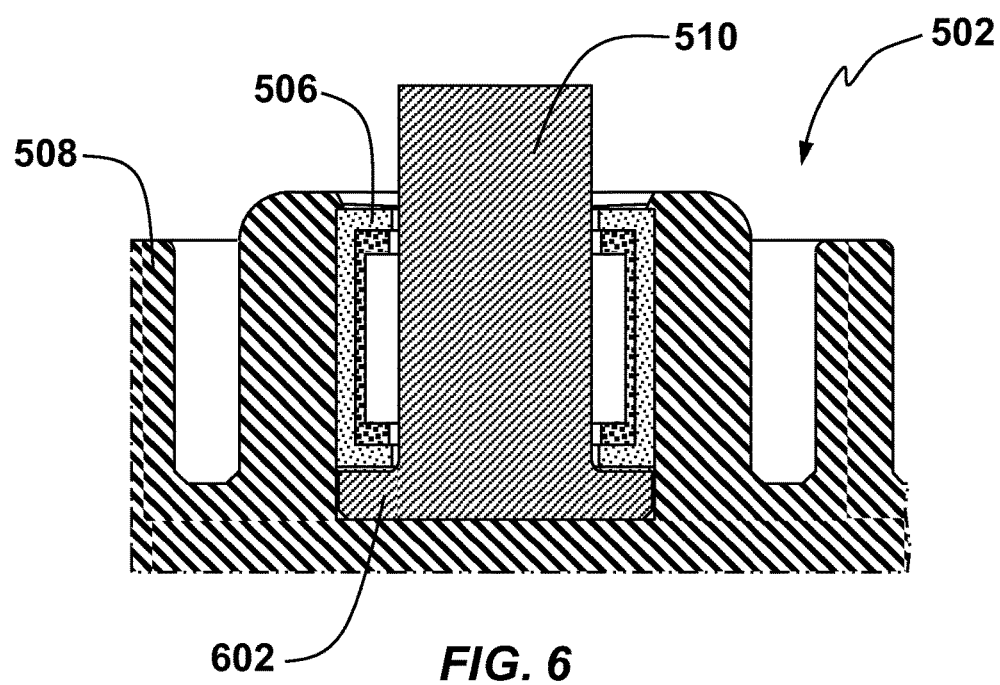
FIG. 6 illustrates a cross sectional view of the ratchet mechanism of the example compression device illustrated in FIG. 5.

FIG. 6 illustrates a cross sectional view of the ratchet mechanism 506. The shaft 510 can include a lip 602 that prevents the shaft 510 from being removed from the compression device 106. In some implementations, a thin film of Teflon can rest between the bottom of the lip 602 and the puck 502 to reduce the friction between the shaft 510 and the puck 502 when the shaft 510 rotates. The ratchet mechanism 506, shaft 510, lip 602, or any combination thereof can be greased to reduce friction.

Figure 7:
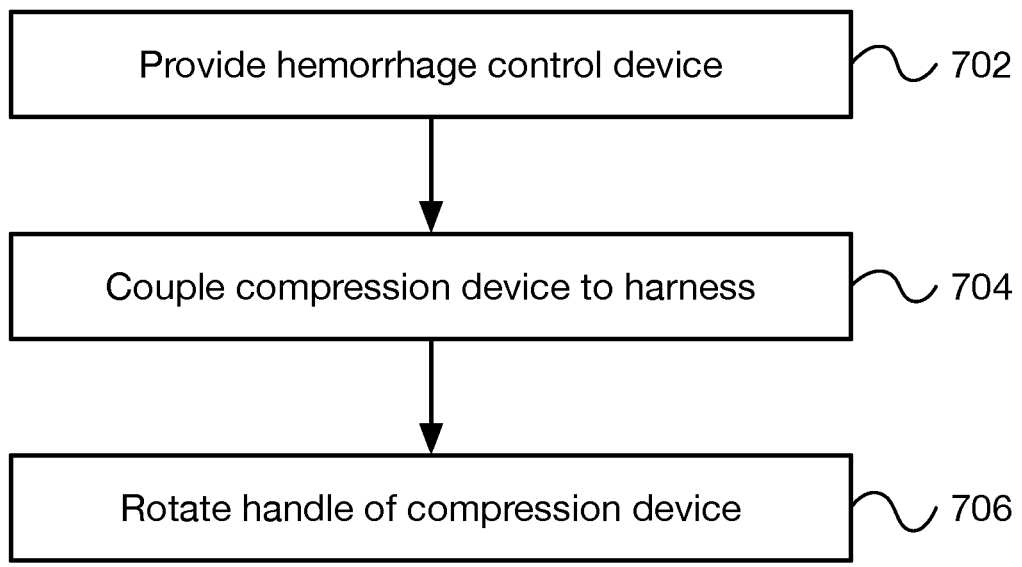
FIG. 7 illustrates a flow diagram of an example method for controlling a hemorrhage using the system illustrated in FIG. 1.

FIG. 7 illustrates a flow diagram of an example method 700 for controlling a hemorrhage using the devices described herein. The method 700 includes providing a hemorrhage control device (step 702). A compression device of the hemorrhage control device is coupled to a harness of the hemorrhage control device (step 704). A handle of the hemorrhage control device is then rotated to apply a compressive and constrictive force to the wearer of the hemorrhage control device (step 706).

As set forth above, the example method 700 includes providing a hemorrhage control device (step 702). The hemorrhage control device can be any of the hemorrhage control devices described herein. With reference to FIG. 1, the hemorrhage control device can include a harness 102 and at least one compression device 106. The harness 102 can be worn by the wearer 104 prior to the need to control a hemorrhage. For example, a soldier may wear the harness 102 as part of everyday combat dress. The harness 102 can be configured to be worn around at least one upper junctional area, such as where the wearer's arms join to the wearer's trunk, and at least one lower junctional area, such as where the wearer's legs join to the wearer's trunk. In some implementations, the harness 102 can be configured to only be worn around upper or lower junctional areas at a given time. The hemorrhage control device also includes at least one compression device 106 that is configured to reversibly couple with the harness 102. The compression device 106 includes a compression puck that is configured to apply pressure to the wearer. The compression device 106 also includes a handle that can be tightened around the harness 102, and a ratchet mechanism that enables the handle to rotate in substantially only one direction.

The method 700 also includes coupling the handle of the compression device to the harness (step 704). The compression device may be coupled to the harness near the junctional area nearest the injury. For example, if a solider is injured in the left leg, the compression device may be coupled to the harness near the wearer's left lower junctional area. The compression device can be coupled to the harness such that when the hemorrhage control device applies pressure to the wearer, the pressure can substantially stop blood flow to the sight of the injury. In some implementations, the handle of the compression device is coupled to the harness by placing the compression device under the harness (e.g., between the harness and the wearer) such that the harness runs across the handle of the compression device. The handle can then be rotated to spool the harness around the handle (or shaft thereof). In some implementations, the harness includes a plurality of MOLLE loops. The handle of the compression device can be inserted through one or more of the MOLLE loops and then rotated. In other implementations, the harness can include other types of attachment points in place of, or in addition to, the MOLLE loops such as other types of loops or rings.

The method 700 also includes rotating the handle of the hemorrhage control device to apply a compressive and constrictive force to the wearer of the hemorrhage control device (step 706). As the user, which can be the wearer or another individual, rotates the handle, the harness spools around the handle of the compression device—creating a windlass mechanism. The above described ratchet mechanism of the compression device prevents the handle from rotating in the opposite direction and unspooling the harness. As the handle is rotated and the harness spools around the handle, the reduction in slack of the harness around the junctional area of the wears constricts the harness around the junctional area. Concurrently, the constriction of the harness about the junctional area depresses the compression device into the junctional area of the wearer. The depressive pressure exerted by the compression device and the constrictive pressure exerted by the harness can cause arteries and veins running through the junctional area to collapse and occlude, which substantially prevents blood flow through the arteries and veins running through the junctional area.

Figure 8:
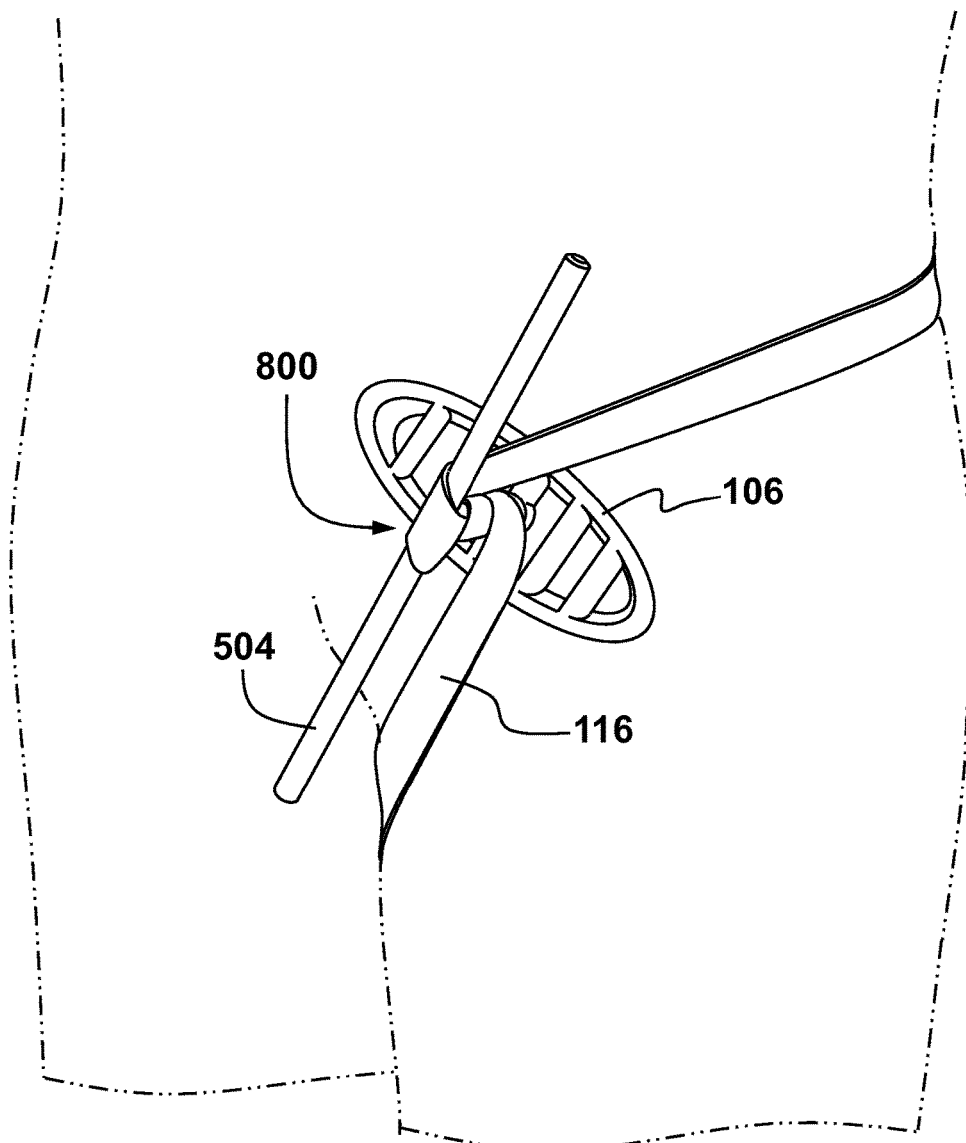
FIG. 8 illustrates the use of the system illustrated in FIG. 1 according the method illustrated in FIG. 7.

FIG. 8 illustrates the rotation of the handle of the hemorrhage control device to apply a compressive and constrictive force to the wearer of the hemorrhage control device as described above in relation to step 706 of FIG. 7. As described above, the compression device 106 was placed between the wearer and the harness. As illustrated in FIG. 8, the compression device 106 was placed under one of the leg strap 116 of the harness. The compression device 106 is placed over a lower junctional area that includes the femoral artery. The wearer of the hemorrhage control device has performed several rotations of the handle 504, which causes the leg strap 116 to spool around the handle 504 and shaft thereof a point 800. The spooling of the leg strap 116 around the handle 504 constricts the leg strap 116 around the wearer's leg and lower junctional area. The constriction of the leg strap 116 also depresses the compression device 106 toward the lower junctional area and the femoral artery.

The disclosed system and methods may be embodied in other specific forms without departing from the spirit or essential characteristics thereof. The forgoing implementations are therefore to be considered in all respects illustrative, rather than limiting of the invention.

What is claimed:

1. A hemorrhage control device comprising:
   a harness configured to be worn around an upper junctional area and a lower junctional area of a user; and
   a compression device comprising a compression puck and a handle extending from the compression puck, wherein the compression device is positionable at the upper junctional area and the lower junctional area and the compression device configured to detachably couple with the harness, the compression device comprising:
      the compression puck configured to apply a pressure to at least one of a portion of the upper junctional area and a portion of the lower junctional area; and
      the handle configured to constrict the harness around the one of the upper junctional area and the lower junctional area.

2. The device of claim 1, further comprising a ratchet mechanism configured to enable the handle to rotate in substantially only one direction.

3. The device of claim 2, wherein the ratchet mechanism comprises a roller bearing.

4. The device of claim 1, wherein the harness further comprises one or more modular lightweight load-carrying equipment (MOLLE) loops.

5. The device of claim 4, wherein the handle is configured to detachably couple to the one or more MOLLE loops.

6. The device of claim 1, wherein the handle is configured to constrict the harness with a windlass mechanism.

7. The device of claim 1, wherein the handle is detachably coupled to the compression puck.

8. The device of claim 1, further comprising a second compression device configured to detachably couple with the harness.

9. The device of claim 1, wherein the compression puck comprises at least one of acrylonitrile butadiene styrene (ABS) plastic, aluminum, stainless steel, carbon fiber, and polyether ether ketone (PEEK).

10. The device of claim 1, wherein a bottom surface of the compression puck is textured.

* * * * *